(12) United States Patent
Song et al.

(10) Patent No.: US 6,174,541 B1
(45) Date of Patent: Jan. 16, 2001

(54) SKIN AGING AND WOUND TREATMENT USING CELL MIGRATION AGENTS

(76) Inventors: Jin Song, 13525 Denton Dr., Dallas, TX (US) 75234; John Koch, 8343 Deep Green Dr., Dallas, TX (US) 75249; Marilyn Squier, 614 Reniosa, Garland, TX (US) 75043

( * ) Notice: Under 35 U.S.C. 154(b), the term of this patent shall be extended for 0 days.

(21) Appl. No.: 09/273,681

(22) Filed: Mar. 22, 1999

Related U.S. Application Data

(63) Continuation of application No. PCT/US98/13675, filed on Jun. 30, 1997.

(51) Int. Cl.[7] .............................. A61F 2/02; A61F 13/02; A61K 9/48; A61K 9/20
(52) U.S. Cl. .................... 424/423; 424/434; 424/435; 424/443; 424/451; 424/464
(58) Field of Search ................................... 424/423, 443, 424/451, 464, 434, 435

(56) References Cited

U.S. PATENT DOCUMENTS 4,847,283 * 7/1989 Harendza-Harinxma .

* cited by examiner

*Primary Examiner*—Carlos A. Azpuru
(74) *Attorney, Agent, or Firm*—David W. Carstens; Carstens, Yee & Cahoon, L.L.P.

(57) ABSTRACT

A cell migration agent promotes the healing of wounds by promoting movement of fibroblast cells away from the periphery of the wound. The agents can include Indole-3-Acetic acid and its derivatives such as Indole-3-Acetyl-L-Phenylalanine. Significant increases in the migration of fibroblast cells were observed at five days after treatment initiation. When administered in a dosage of between 0.1 and 250 ppm, these compounds appear to have the ability to move healthy human fibroblast cells into areas void of cells more rapidly than if the agent were not present. This results in the plumping of the skin or healing of wounds. The compounds can be delivered by topical or internal methods of application.

37 Claims, 2 Drawing Sheets

SKIN AGING AND WOUND TREATMENT USING CELL MIGRATION AGENTS

This application claims Priority from PCT/US98/13,675 filed Jun. 30, 1997.

TECHNICAL FIELD OF THE INVENTION

The present invention relates to a plant derived cell migration agent, such as Indole-3-Acetic acid, that facilitates the healing of tissue such as skin. The cell migration agent is useful in treating wrinkled skin and can minimize the effects of photo aging on the skin by itself, or in conjunction with alpha-hydroxy acid (AHA), retinoic acid, or other chemical peel agents.

BACKGROUND OF THE INVENTION

Human tissue can be damaged in numerous ways. For example, the skin can be burned by the sun or the application of acids such as alpha-hydroxy acid (AHA). Muscle tissue can suffer damage from a lack of oxygen or from traumatic injury. In either case, the body produces a certain healing response. It has been proposed that the speed of healing of tissue damage is improved with the application of a cell migration agent. Cell migration agents generally promote the migration of fibroblast cells from the periphery of the wounded tissue to a location inside the wounded area. Fibroblast cells are mesenchyme cells which give rise to connective tissue. For purposes of this discussion, a wound includes any damage to tissue from any source. During the normal healing process, the tissue, such as skin, heals inward from the peripheral edge of the wound. Improved healing speed has been observed when fibroblast cells migrate to the middle of the wound and heal outward to meet the inward progression from the periphery.

It has been proposed that the plant hormones or growth factors might also play an important role in the healing of wounded animal tissue. Certain compounds appear to improve the growth of plant cells including gibberellins, indolacetic acid and kinetin. For example, U.S. Pat. No. 5,188,655 to Jones et al. discloses a plant growth enhancing composition comprising as an active ingredient a synergistic mixture of (a) gibberellins, (b) the heteroauxin indole-3-acetic acid and the cytokinin 6-(4-hydroxy-3-methyl-2-trans-betenylamino) purine. These plant growth enhancing agents have very low molecular weights typically between 175 and 346. There has been no correlation between the use of plant growth hormones and wound healing in human cell studies.

A need exists for a plant derived cell migration agent that can be used to improve the healing of animal tissue. Such a cell migration agent should be useful for human application with particular benefits in healing skin. Skin damage can include aging from sun or chemical exposure. Therefore, a suitable cell migration agent should be useful in minimizing or healing skin damage associated with aging and sun or chemical exposure.

SUMMARY OF THE INVENTION

A study involving human cells and plant growth enhancing agents has shown that Indole-3-Acetic acid (also known as "Auxin") and its derivatives significantly increases the migration of fibroblast cells at five days after treatment initiation. Derivatives such as Indole-3-Acetyl-L-Phenylalanine have shown improved cell migration results. Likewise, derivatives such as Indole-3-Acetic Acid Methyl Ester, Indole-3-Acetyl-L-Alanine, Indole-3-Acetyl-L-Aspartic Acid, and Indole-3-Acetylglycine should produce similar beneficial results.

Auxin and its derivative Indole-3-Acetyl-L-Phenylalanine maintained increased migration rates throughout the study. When administered in a dosage of at least 0.1 ppm, these compounds appear to have the ability to move healthy human fibroblast cells into areas void of cells more rapidly than if the agent were not present. Dosage levels of between 2 and 250 ppm showed better results. Once migrated, the healthy cells can then divide at their normal rate thus effectively filling the voided area quicker. This results in the plumping of the skin or healing of wounds. The compounds can be delivered by topical or internal methods of application.

DESCRIPTION OF THE DRAWINGS

For a more complete understanding of the present invention, and for further details and advantages thereof, reference is now made to the following Detailed Description taken in conjunction with the accompanying drawings, in which.

DETAILED DISCUSSION OF THE DRAWINGS

Figure 1:
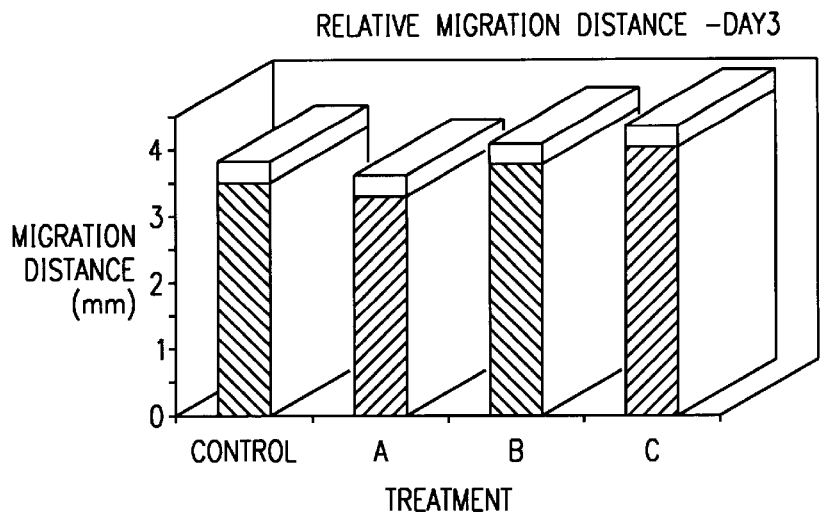
FIG. 1 is a bar chart showing the observed relative cell migration distances under the effect of three compounds under test for three days.
Figure 2:
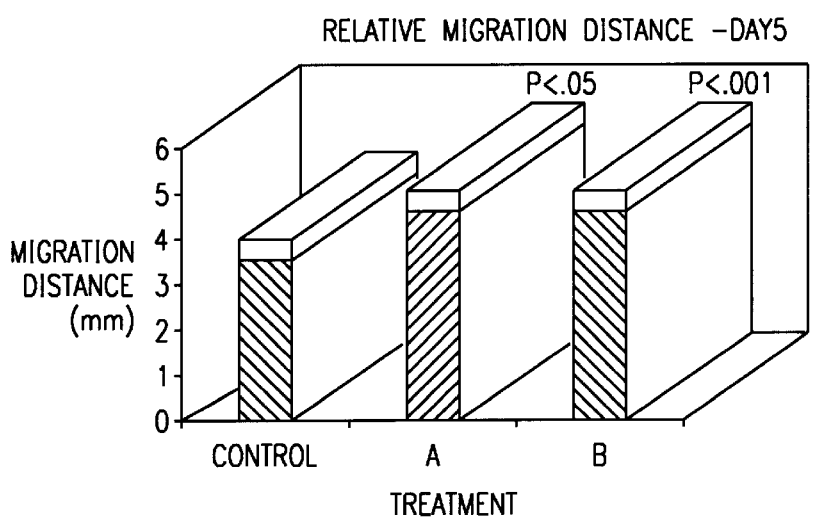
FIG. 2 is a bar chart showing the observed relative cell migration distances under the effect of three compounds under test for five days.
Figure 3:
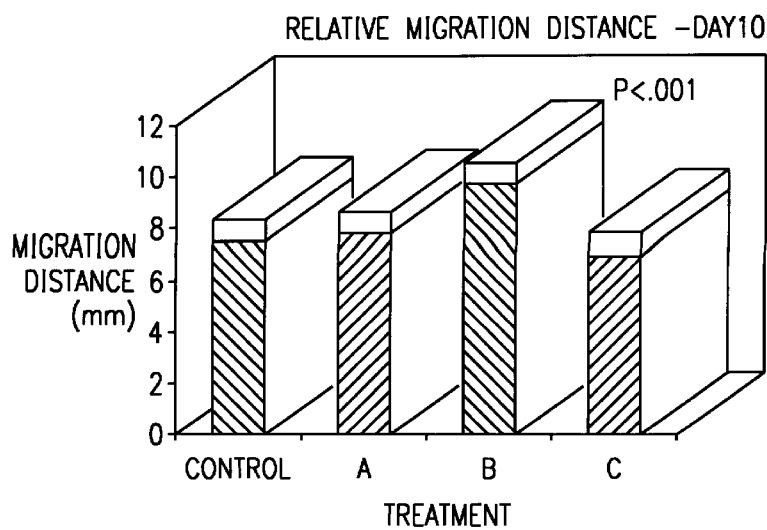
FIG. 3 is a bar chart showing the observed relative cell migration distances under the effect of three compounds under test for ten days.
Figure 4:
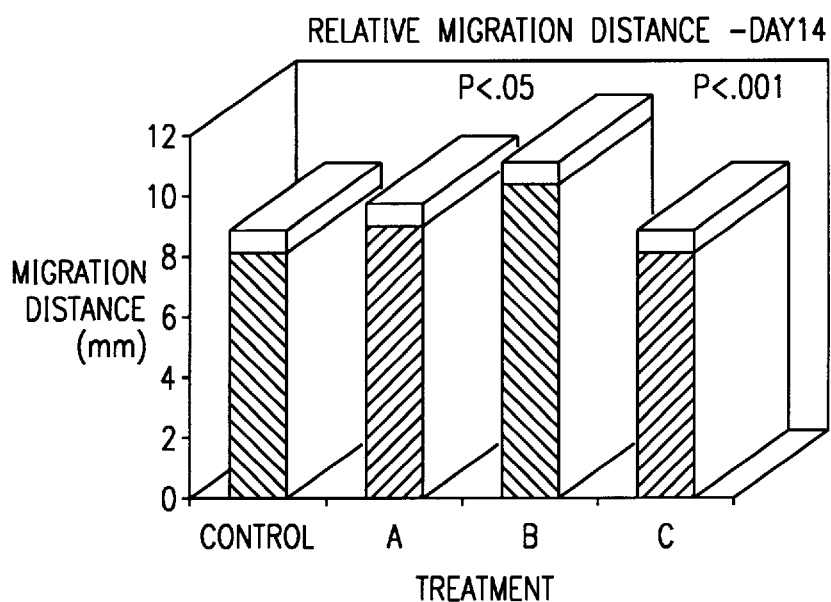
FIG. 4 is a bar chart showing the observed relative cell migration distances under the effect of three compounds under test for fourteen days.

Improved wound healing has been observed with the use of Indole-3-Acetyl-L-Phenylalanine and Indole-3-Acetic acid. To verify these observations a study was conducted. The initial intent of these studies was to determine the possible cell growth promoting (mitogenic) activity of three plant-derived agents reported to promote wound healing in a small pilot study. The agents, blindly labeled A, B, and C; were tested at various concentrations to see if any had any mitogenic activity. Concentrations of 0, 1, 1, 10, 25, 50, 100, and 250 ppm were tested. Agent A was a compound containing Indole-3-Acetic acid. Agent B was a compound containing Indole-3-Acetyl L-Phenylanine. Agent C was a compound containing gibberellic acid. Agent A was significantly inhibitory and agent B was mildly inhibitory of fibroblast cell growth. Fibroblasts are the chief cell of interest for these studies due to their central role in wound healing. Agent C had no significant influence on cell growth. The agents could be administered by injection, topical application, ingestion or inhalation.

These findings led to the postulation that the agents were instead promoting cell migration into the wound area, rather than cell growth. This hypothesis is based upon the fact that the initial phase of either cutaneous or vascular wound healing is cell migration into the wounded area rather than cell division to replace the lost or injured cells. To test this possibility that any one or more of these agents might contribute to wound healing by stimulating cell migration, an in vitro wound model was developed. Skin fibroblasts were initially seeded in 60 mm diameter round culture dishes and allowed to grow until they covered the plate bottom in the presence of their normal growth medium. Upon attaining this confluence, a small circular area of cells of approximately 25 mm diameter was removed by scraping from the center of each plate. At this point the remaining cells were fed with a nutrient culture medium devoid of any added growth factors (which can act to stimulate cell migration). To this medium was added either a small amount of ethanol (used as a vehicle for drug administration) alone (control) or containing 250 ppm of either A,B, or C. Cells were refed with the respective medium every three days to maintain relatively constant drug levels within the media. The exact edge of the wound area was demarcated in black and migration distance was measured as the distance from that perimeter to the farthest cell inside the wound area using an inverted phase light microscope. Five measurements were taken around the perimeter of each wound area on days 3, 5, 10, and 14. Distances of fibroblast migration in response to agents A,B, and C were compared as presented in FIGS. 1, 2, 3 and 4. Most averages presented represent an average of 25 replicates (n=25). Treatment groups were statistically compared using Student's unpaired t-analysis. The results as represented in FIGS. 1 to 4 indicate that agent B consistently and significantly increased fibroblast cell migration relative to cells treated with control media alone starting at day 5 after treatment initiation. Cells treated with agent A also showed a small but significant increase in cell migration relative to control cells at days 5 and 14.

Figure 5:
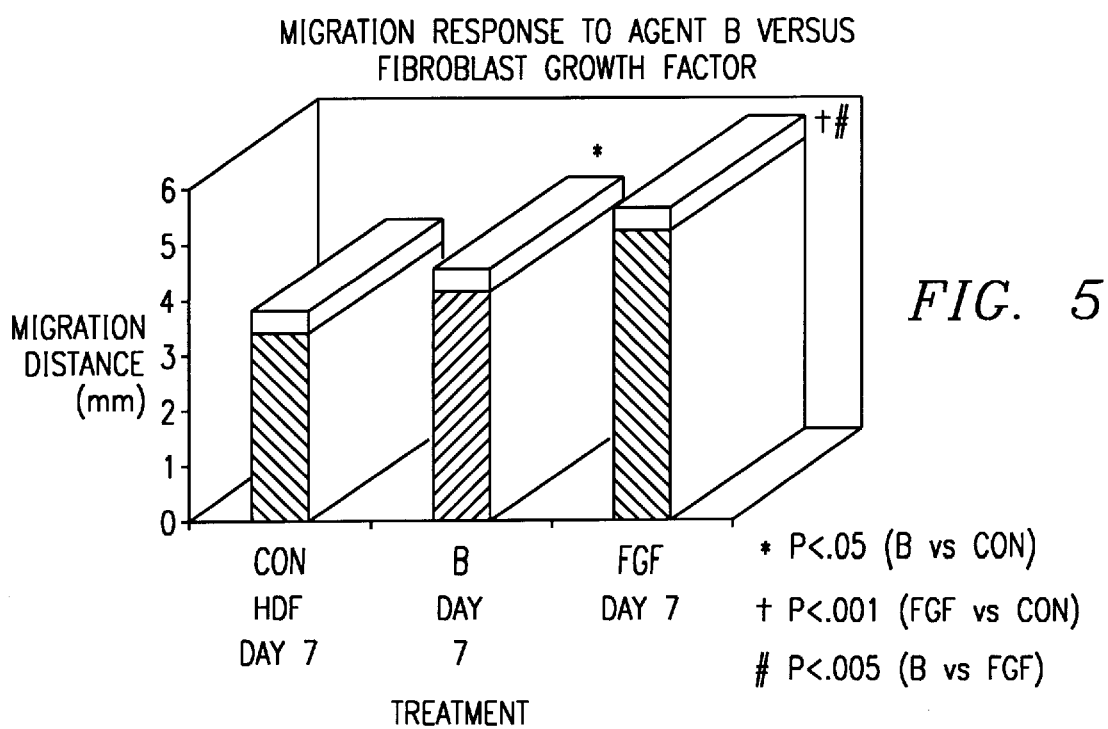
FIG. 5 is a bar chart showing the migration response of Agent B versus fibroblast growth factor.

The consistency and level of response to agent B stimulated the question as to its relative potency compared to an agent known to maximally stimulate fibroblast migration. Therefore, a comparison was made between fibroblast growth factor (FGF) and Agent B. FGF was used based on its well documented ability to stimulate fibroblast cell migration. FIG. 5 illustrates that Agent B again increased cell migration but not as strongly as FGF (20 ng/ml). Specifically, the average migration at 7 days for B-treated cells was 4.1±0.37 mm compared to 5.3±0.24 mm for control cells. Comparatively, this data indicates that Agent B elicited about one-third the migratory response that was observed in response to FGF.

In conclusion, none of these agents are mitogenic and two are actually inhibitory of cell mitogenics (or cell growth). On the other hand, agents A and B had significant effects to stimulate fibroblast cell migration. The fact that these agents are not mitogenic may be a positive characteristic in terms of an agent that might be therapeutically applied. Thus, a mitogenic agent might provoke concerns relative to its potential effects as a carcinogen. The stimulation of migration by agents A and B raise the possibility that it may be an effective agent in promoting wound healing. Thus, Agents A and B should reduce the signs of skin aging.

Although preferred embodiments of the present invention have been described in the foregoing Detailed Description and illustrated in the accompanying Figures, it will be understood that the invention is not limited to the compounds disclosed, but is capable of numerous variations in composition without departing from the spirit of the invention. Accordingly, the present invention is intended to encompass such variations as fall within the scope of the claims.

We claim:

1. A method of promoting the healing of a tissue wound comprising delivering a therapeutically effective dosage of Indole-3-Acetic-Acid or its derivatives wherein said dosage promotes the migration of cells into a damaged cellular area.

2. The method of claim 1 wherein said step of delivering comprises topical application of the dosage.

3. The method of claim 1 wherein said step of delivering comprises injection of the dosage.

4. The method of claim 1 wherein said step of delivering comprises ingestion of the dosage.

5. The method of claim 1 wherein said step of delivering comprises inhalation of the dosage.

6. The method of claim 1 wherein said step of delivering a therapeutically effective dosage comprises delivering Indole-3-Acetyl-L-Phenylalanine.

7. The method of claim 1 wherein said step of delivering a therapeutically effective dosage comprises delivering Indole-3-Acetyl-L-Acetylglycine.

8. The method of claim 1 wherein said step of delivering a therapeutically effective dosage comprises delivering Indole-3-Acetyl-L-Aspartic Acid.

9. The method of claim 1 wherein said step of delivering a therapeutically effective dosage comprises delivering Indole-3-Acetyl-L-Alanine.

10. The method of claim 1 wherein said step of delivering a therapeutically effective dosage comprises delivering Indole-3-Acetic Acid Methyl Ester.

11. The method of claim 10 wherein said step of delivering a therapeutically effective dosage comprises delivering between 0.1 and 1000 ppm of the Indole-3-Acetic Acid or its derivatives.

12. The method of claim 10 wherein said step of delivering a therapeutically effective dosage comprises delivering between 0.10 and 250 ppm of the Indole-3-Acetic Acid or its derivatives.

13. The method of claim 1 wherein said step of delivering a therapeutically effective dosage further comprises delivering a chemical peel agent.

14. A method of promoting the healing of tissue comprising the step of delivering a therapeutically effective dosage of Indole-3-Acetic-Acid or its derivatives wherein said dosage promotes the migration of cells into a damaged cellular area wherein said cellular damage are wrinkles.

15. The method of claim 14 wherein said step of delivering a therapeutically effective dosage comprises delivering Indole-3-Acetyl-L-Phenylalanine.

16. The method of claim 14 wherein said step of delivering a therapeutically effective dosage comprises delivering Indole-3-Acetyl-L-Acetylglycine.

17. The method of claim 14 wherein said step of delivering a therapeutically effective dosage comprises delivering Indole-3-Acetyl-L-Aspartic Acid.

18. The method of claim 14 wherein said step of delivering a therapeutically effective dosage comprises delivering Indole-3-Acetyl-L-Alanine.

19. The method of claim 14 wherein said step of delivering a therapeutically effective dosage comprises delivering Indole-3-Acetic Acid Methyl Ester.

20. The method of claim 14 wherein said step of delivering a therapeutically effective dosage comprises delivering between 0.1 and 1000 ppm of the Indole-3-Acetic Acid or its derivatives.

21. The method of claim 14 wherein said step of delivering a therapeutically effective dosage comprises delivering between 0.10 and 250 ppm of the Indole-3-Acetic Acid or its derivatives.

22. The method of claim 14 wherein said step of delivering a therapeutically effective dosage further comprises delivering a chemical peel agent.

23. The method of claim 14 wherein the step of delivering comprises topical application of the dosage.

24. The method of claim 14 wherein the step of delivering comprises injection of the dosage.

25. The method of claim 15 wherein the step of delivering comprises ingestion of the dosage.

26. A method of promoting the healing of a tissue wound comprising delivering a therapeutically effective dosage of Indole-3-Acetic-Acid or its derivatives wherein said dosage promotes the migration of cells into a damaged cellular area wherein said cellular damage is a wound.

27. The method of claim 26 wherein said step of delivering a therapeutically effective dosage comprises delivering Indole-3-Acetyl-L-Phenylalanine.

28. The method of claim 26 wherein said step of delivering a therapeutically effective dosage comprises delivering Indole-3-Acetyl-L-Acetylglycine.

29. The method of claim 26 wherein said step of delivering a therapeutically effective dosage comprises delivering Indole-3-Acetyl-L-Aspartic Acid.

30. The method of claim 26 wherein said step of delivering a therapeutically effective dosage comprises delivering Indole-3-Acetyl-L-Alanine.

31. The method of claim 26 wherein said step of delivering a therapeutically effective dosage comprises delivering Indole-3-Acetic Acid Methyl Ester.

32. The method of claim 26 wherein said step of delivering a therapeutically effective dosage comprises delivering between 0.1 and 1000 ppm of the Indole-3-Acetic Acid or its derivatives.

33. The method of claim 26 wherein said step of delivering a therapeutically effective dosage comprises delivering between 0.10 and 250 ppm of the Indole-3-Acetic Acid or its derivatives.

34. The method of claim 26 wherein said step of delivering a therapeutically effective dosage further comprises delivering a chemical peel agent.

35. The method of claim 26 wherein the step of delivering comprises topical application of the dosage.

36. The method of claim 26 wherein the step of delivering comprises injection of the dosage.

37. The method of claim 26 wherein the step of delivering comprises ingestion of the dosage.

* * * * *

UNITED STATES PATENT AND TRADEMARK OFFICE
CERTIFICATE OF CORRECTION

PATENT NO. : 6,174,541 B1  
DATED : January 16, 2001  
INVENTOR(S) : Jin Song, John Koch, Marilyn Squier Page 1 of 1

It is certified that error appears in the above-identified patent and that said Letters Patent is hereby corrected as shown below:

Column 2,
Line 49, after "of", change "0,1" to -- 0.1 --.

Column 4,
Line 24, after the word "claim", change "10" to -- 1 --.
Line 28, after the word "claim", change "10" to -- 1 --.

Column 5,
Line 3, after the word "claim", change "15" to -- 14 --

Signed and Sealed this

Sixth Day of November, 2001

Attest:

NICHOLAS P. GODICI
*Attesting Officer*  *Acting Director of the United States Patent and Trademark Office*